(12) United States Patent
Chono et al.

(10) Patent No.: US 11,935,328 B2
(45) Date of Patent: Mar. 19, 2024

(54) IMAGE PICK-UP APPARATUS, METHOD, SYSTEM, AND COMPUTER READABLE MEDIUM

(71) Applicant: NEC Corporation, Tokyo (JP)

(72) Inventors: Keiichi Chono, Tokyo (JP); Takahiro Toizumi, Tokyo (JP); Masato Tsukada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 80 days.

(21) Appl. No.: 17/431,535

(22) PCT Filed: Feb. 12, 2020

(86) PCT No.: PCT/JP2020/005217
§ 371 (c)(1),
(2) Date: Aug. 17, 2021

(87) PCT Pub. No.: WO2020/170892
PCT Pub. Date: Aug. 27, 2020

(65) Prior Publication Data
US 2022/0139110 A1    May 5, 2022

(30) Foreign Application Priority Data
Feb. 18, 2019    (JP) ................. 2019-026937

(51) Int. Cl.
*G06V 40/19*    (2022.01)
*G06V 10/25*    (2022.01)
(Continued)

(52) U.S. Cl.
CPC .............. *G06V 40/19* (2022.01); *G06V 10/25* (2022.01); *G06V 40/67* (2022.01); *H04N 23/90* (2023.01)

(58) Field of Classification Search
CPC ........ G06V 40/19; G06V 10/25; G06V 40/67; H04N 23/90; H04N 23/80; H04N 5/23229; H04N 5/247
See application file for complete search history.

(56) References Cited

U.S. PATENT DOCUMENTS 7,925,059 B2 *    4/2011    Hoyos ................. G06V 40/19
                                                                    382/117
8,085,993 B2 *    12/2011    Jacobson ............... G06V 10/94
                                                                    382/116
(Continued)

FOREIGN PATENT DOCUMENTS

CN    101154264 A        4/2008
CN    101185101 A *    5/2008    ......... G06K 9/00604
(Continued)

OTHER PUBLICATIONS

S. Venugopalan et al., "Long range iris acquisition system for stationary and mobile subjects," 2011 International Joint Conference on Biometrics (IJCB), 2011, pp. 1-8, doi: 10.1109/IJCB.2011.6117484. (Year: 2011).*

(Continued)

*Primary Examiner* — Michael Robert Cammarata (57) ABSTRACT

Iris image pick-up devices have the same field of view and are disposed at mutually different positions. An overall image pick-up device performs image pick-up over a wide field of view. A guiding device guides a subject. An illumination device illuminates the subject with light. The controller controls, using an image from the overall image pick-up device, at least one of reading out an image from the iris image pick-up devices, presenting at least of an image and a sound through the guiding device, or providing illumination with light from the illumination device.

9 Claims, 5 Drawing Sheets

(51) Int. Cl.
   *G06V 40/60*   (2022.01)
   *H04N 23/90*   (2023.01)

(56) References Cited

U.S. PATENT DOCUMENTS

| | | | | |
|---|---|---|---|---|
| 8,121,356 | B2* | 2/2012 | Friedman | G06V 40/166 |
| | | | | 382/103 |
| 8,213,782 | B2* | 7/2012 | Jelinek | G03B 13/36 |
| | | | | 396/153 |
| 8,433,103 | B2* | 4/2013 | Friedman | G06V 40/19 |
| | | | | 382/116 |
| 8,705,808 | B2* | 4/2014 | Determan | G06V 40/19 |
| | | | | 382/117 |
| 8,957,956 | B2* | 2/2015 | Determan | H04N 23/676 |
| | | | | 348/78 |
| 9,095,287 | B2* | 8/2015 | Hanna | A61B 3/14 |
| 9,336,439 | B2* | 5/2016 | Savvides | G06V 40/19 |
| 11,205,071 | B2* | 12/2021 | Ma | G06V 10/267 |
| 11,539,872 | B2* | 12/2022 | Chono | H04N 23/671 |
| 2005/0084179 | A1* | 4/2005 | Hanna | G06V 40/19 |
| | | | | 382/294 |
| 2007/0160265 | A1* | 7/2007 | Wakiyama | G06V 40/19 |
| | | | | 382/117 |
| 2008/0199054 | A1 | 8/2008 | Matey | |
| 2009/0041309 | A1* | 2/2009 | Kim | G06V 40/19 |
| | | | | 382/117 |
| 2011/0304721 | A1* | 12/2011 | Determan | H04N 23/676 |
| | | | | 348/78 |
| 2014/0313308 | A1* | 10/2014 | Wang | G06V 10/145 |
| | | | | 348/78 |
| 2015/0256741 | A1 | 9/2015 | Towal et al. | |
| 2022/0139114 | A1* | 5/2022 | Chono | G06V 40/197 |
| | | | | 382/117 |
| 2022/0360705 | A1* | 11/2022 | Ogino | G06V 40/19 |

FOREIGN PATENT DOCUMENTS

| | | | | | |
|---|---|---|---|---|---|
| CN | 101520838 | A | * | 9/2009 | |
| CN | 110956054 | A | * | 4/2020 | |
| CN | 113190115 | B | * | 11/2022 | G06K 9/00597 |
| DE | 102018006393 | A1 | | 2/2020 | |
| EP | 4099280 | A1 | * | 12/2022 | G06F 3/013 |
| JP | 2006-163683 | A | | 6/2006 | |
| JP | 2008-158046 | A | | 7/2008 | |
| JP | 2017-517165 | A | | 6/2017 | |
| KR | 100869998 | B1 | * | 11/2008 | |
| SG | 11202108901P | A | | 9/2021 | |
| SG | 11202108903R | A | | 9/2021 | |
| WO | 2009/016846 | A1 | | 2/2009 | |
| WO | WO-2009016846 | A1 | * | 2/2009 | |
| WO | 2016/041444 | A2 | | 3/2016 | |

OTHER PUBLICATIONS

J. R. Matey et al., "Iris on the Move: Acquisition of Images for Iris Recognition in Less Constrained Environments," in Proceedings of the IEEE, vol. 94, No. 11, pp. 1936-1947, Nov. 2006, doi: 10.1109/JPROC.2006.884091. (Year: 2006).*

J. A. De Villar, R. W. Ives and J. R. Matey, "Design and implementation of a long range iris recognition system," 2010 Conference Record of the Forty Fourth Asilomar Conference on Signals, Systems and Computers, 2010, pp. 1770-1773, doi: 10.1109/ACSSC.2010.5757845. (Year: 2010).*

C. Boehnen, D. Barstow, D. Patlolla and C. Mann, "A multi-sample standoff multimodal biometric system," 2012 IEEE Fifth International Conference on Biometrics: Theory, Applications and Systems (BTAS), 2012, pp. 127-134, doi: 10.1109/BTAS.2012.6374567. (Year: 2012).*

F. Bashir, P. Casaverde, D. Usher and M. Friedman, "Eagle-Eyes: A System for Iris Recognition at a Distance," 2008 IEEE Conference on Technologies for Homeland Security, 2008, pp. 426-431, doi: 10.1109/THS.2008.4534490. (Year: 2008).*

Xiaokun Li, Genshe Chen, Qiang Ji and E. Blasch, "A non-cooperative long-range biometric system for maritime surveillance," 2008 19th International Conference on Pattern Recognition, 2008, pp. 1-4, doi: 10.1109/ICPR.2008.4761887. (Year: 2008).*

Kwon (Kwon KA, Shipley RJ, Edirisinghe M, Ezra DG, Rose G, Best SM, Cameron RE. High-speed camera characterization of voluntary eye blinking kinematics. J R Soc Interface. Jun. 12, 2013;10(85):20130227. doi: 10.1098/rsif.2013.0227. PMID: 23760297; PMCID: PMC4043155.) (Year: 2013).*

Azmi (Diyanah Inani Azmi, Hafazah Abdul Karim, Mohd Zamreen Mohd Amin, Comparing the Walking Behaviour between Urban and Rural Residents, Procedia—Social and Behavioral Sciences, vol. 68, 2012, pp. 406-416, ISSN 1877-0428, https://doi.org/10.1016/j.sbspro.2012.12.237). (Year: 2012).*

J. A. De Villar, R. W. Ives and J. R. Matey, "Design and implementation of a long range iris recognition system," 2010 Conference Record of the Forty Fourth Asilomar Conference on Signals, Systems and Computers, Pacific Grove, CA, USA, 2010, pp. 1770-1773, doi: 10.1109/ACSSC.2010.5757845. (Year: 2010).*

International Search Report for PCT Application No. PCT/JP2020/005217, dated Apr. 28, 2020.

Masahiko Hosoya, "Identification System by Iris Recognition". Transactions of the Japanese Society for Medical and Biological Engineering 44(1), pp. 33-39. 2006.

John Daugman, "How Iris Recognition Works", pp. 1-10, [Online] <URL: https://www.cl.cam.ac.uk/~jgd1000/irisrecog.pdf>.

Extended European Search Report for EP Application No. 20758565.4 dated Mar. 17, 2022.

Kang Ryoung Park: "New Automated Iris Image Acquisition Method", Applied Optics, Optical Society of America, vol. 44, No. 5, pp. 713-734, Feb. 10, 2005, XP008056591.

Indian Office Action for IN Application No. 202147041266 dated Aug. 5, 2022.

Singapore Office Action for SG Application No. 11202108917P dated Feb. 20, 2023.

CN Office Action for CN Application No. 202080022128.1, dated Jan. 12, 2024 with English Translation.

* cited by examiner

IMAGE PICK-UP APPARATUS, METHOD, SYSTEM, AND COMPUTER READABLE MEDIUM

This application is a National Stage Entry of PCT/JP2020/005217 filed on Feb. 12, 2020, which claims priority from Japanese Patent Application 2019-026937 filed on Feb. 18, 2019, the contents of all of which are incorporated herein by reference, in their entirety.

TECHNICAL FIELD

The present disclosure relates to an image pick-up apparatus, a method, a system, and a computer readable medium, and in particular to an image pick-up apparatus, a method, a system, and a computer readable media that can be used for photographing an iris(es) of a subject.

BACKGROUND ART

Biometric authentication using an iris(es) has been known. In such biometric authentication, iris(es) of a subject is photographed by using an image pick-up apparatus, and feature values are extracted from the pattern of the photographed iris. In order to authenticate a subject, extracted feature values are compared with those registered in advance in a database, and a pass/fail is determined based on a score of matching therebetween. Further, in order to register a subject to be authenticated, extracted feature values are added in the database.

As described in Non-patent Literature 1, an iris, which is a donut-shaped tissue surrounding a pupil, has a very complex pattern, and is unique to each person. Further, in the photographing of an iris, near-infrared light is applied to eyes of a subject.

As described in Non-patent Literature 2, in the photographing of an iris(es), an image of the iris is taken with a resolution in which the radius of the iris is expressed by 100 to 140 pixels. Further, the wavelength of the near-infrared light applied to the eyes of the subject is in a range between 700 nm and 900 nm.

CITATION LIST

Patent Literature

Patent Literature 1: International Patent Publication No. WO2009/016846

Non Patent Literature

Non-patent Literature 1: Hosoya, "Identification System by Iris Recognition", Japanese Society for Medical and Biological Engineering 44(1), pages 33-39, 2006
Non-patent Literature 2: Daugman, "How Iris Recognition Works," https://www.cl.cam.ac.uk/~jgd1000/irisrecog.pdf

SUMMARY OF INVENTION

Technical Problem

The diameter of an iris is about 1 cm. Therefore, when the radius of an iris is expressed by 100 pixels, the granularity becomes 50 μm. Since the pattern of an iris is microscopic as described above, it is difficult to photograph an iris pattern at a level of quality sufficient for authentication and verification under conditions that distance between the subject and the image pick-up means is large, a field of view to be photographed is wide, and the subject moves.

In light of the above circumstances, an object of the present disclosure is to provide an image pick-up apparatus, method, system, and computer-readable medium capable of photographing an iris pattern at a level of quality sufficient for authentication and verification.

Solution to Problem

In order to achieve the above-described object, in a first aspect, the present disclosure provides an image pick-up system including:

a plurality of iris image pick-up means disposed at mutually different positions in the same field of view;

overall image pick-up means for performing image pick-up over a wider field of view than the field of view of the iris image pick-up means;

guiding means for guiding a subject;

illumination means for illuminating the subject with light; and control means for controlling, using an image from the overall image pick-up means, at least one of reading out an image from the plurality of iris image pick-up means, presenting at least one of an image and a sound through the guiding means, or providing illumination with light from the illumination means, wherein the plurality of iris image pick-up means include a plurality of first iris image pick-up means having a focusing point at a predetermined position and being for performing image pick-up of mutually different regions in a vertical direction, and at least one second iris image pick-up means having a focusing point at a position closer to the first iris image pick-up means than the predetermined position, such that a time difference with respect to a time when the subject passes through the focusing point of the plurality of the first iris image pick-up means is shorter than a blink interval time and longer than a blink duration, and the second iris image pick-up means is disposed between two adjacent first iris image pick-up means.

In a second aspect, the present disclosure provides an image pick-up apparatus including:

iris image pick-up means for performing image pick-up of an iris of a moving subject, wherein the iris image pick-up means includes a plurality of first iris image pick-up means having a focusing point at a predetermined position and being for performing image pick-up of mutually different regions in a vertical direction, and at least one second iris image pick-up means having a focusing point at a position closer to the first iris image pick-up means than the predetermined position, such that a time difference with respect to a time when the subject passes through the focusing point of the plurality of the first iris image pick-up means is shorter than a blink interval time and longer than a blink duration, and the second iris image pick-up means is disposed between two adjacent first iris image pick-up means.

In a third aspect, the present disclosure provides an image pick-up method including:

performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, and providing illumination with light from illumination means for illuminating the subject with light.

In a fourth aspect, the present disclosure provides an image pick-up method including:

performing image pick-up of an iris of a moving subject by using a plurality of first iris image pick-up means having a focusing point at a predetermined position and being for performing image pick-up of mutually different regions in a vertical direction; and performing image pick-up of the iris of the subject by using at least one second iris image pick-up means having a focusing point at a position closer to the first iris image pick-up means than the predetermined position such that a time difference with respect to a time when the subject passes through the focusing point of the plurality of the first iris image pick-up means is shorter than a blink interval time and longer than a blink duration, and disposed between two adjacent first iris image pick-up means.

In a fifth aspect, the present disclosure provides a non-transitory computer readable medium storing a program causing a computer to execute a process including:

performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, and providing illumination with light from illumination means for illuminating the subject with light.

In a sixth aspect, the present disclosure provides a non-transitory computer readable medium storing a program causing a computer to execute a process including:

performing image pick-up of an iris of a moving subject by using a plurality of first iris image pick-up means having a focusing point at a predetermined position and being for performing image pick-up of mutually different regions in a vertical direction; and performing image pick-up of the iris of the subject by using at least one second iris image pick-up means having a focusing point at a position closer to the first iris image pick-up means than the predetermined position such that a time difference with respect to a time when the subject passes through the focusing point of the plurality of the first iris image pick-up is shorter than a blink interval time and longer than a blink duration, and disposed between two adjacent first iris image pick-up means.

Advantageous Effects of Invention

An image pick-up apparatus, a method, a system, and a computer readable medium according to the present disclosure is capable of photographing an iris pattern at a level of quality sufficient for authentication and verification.

DESCRIPTION OF EMBODIMENTS

Prior to giving the description of an example embodiment according to the present disclosure, a problem thereof is quantitively described. As an example, the below-shown conditions, which are assumed as operational conditions for Automated Border Control systems (ABC systems) and the like, will be described hereinafter. It is assumed that a distance between a subject and image pick-up means (the distance between a subject and a gate) is 2 m, and a horizontal field of view, i.e., a range in the horizontal direction in which both eyes of one subject can be covered, is 0.2 m. Further, a vertical field of view, i.e., a range in the vertical direction in which the eyes of a wide range of subjects from a tall subject, typically a male person, to a short subject, typically a female person, can be covered, is 0.4 m. Further, it is assumed that the walking speed (the moving speed) of the subject relative to the gate is equal to the average of slow walking speeds of adult people, e.g., is 1 m/s.

Under the above operating conditions, assuming that an image sensor with a pixel pitch of 5 μm and a lens with an aperture stop of F2 and a focal length of 200 mm are used, both a high resolution of 32 M pixels and a high frame rate of 100 frames per second (fps) are demanded from the image pick-up means, as described later.

With regard to resolution, to secure a 0.2 m horizontal field of view at a position 2 m away from the image pick-up apparatus, the image pick-up apparatus needs 4000 pixels (0.2 [m] 50 [μm]=4000) in the horizontal direction. Further, to secure a 0.4 m vertical field of view at a position 2 m away from the image pick-up apparatus, the image pick-up apparatus needs 8000 pixels (0.4 [m]÷50 [μm]=8000) in the vertical direction. As a result, a resolution of 32 M pixels is demanded from the image pick-up apparatus.

On the other hand, in the case where the above lens is used, if the allowable circle of confusion diameter is 0.03 mm, the depth of field that can be secured 2 m away is approximately 1 cm. In the case where the subject has a walking speed of 1 m/s, the time it takes for the subject to pass through the 1 cm subject depth is 1 [cm]±100 [cm/s]= 0.01 s. In this case, to capture the 0.01 s instant when the iris of the walking subject is in focus, a performance of 100 fps (1 [s]±100 [fps]=0.01 s time resolution) is demanded from the image pick-up apparatus.

Image pick-up equipment capable of satisfying a high resolution of 32 M pixels and a high frame rate of 100 fps with a single device does not exist as a popular product. Consequently, photographing an iris pattern at a level of quality sufficient for authentication and verification under the operating conditions described above is difficult. This concludes the quantitative description of the problem.

Figure 1:
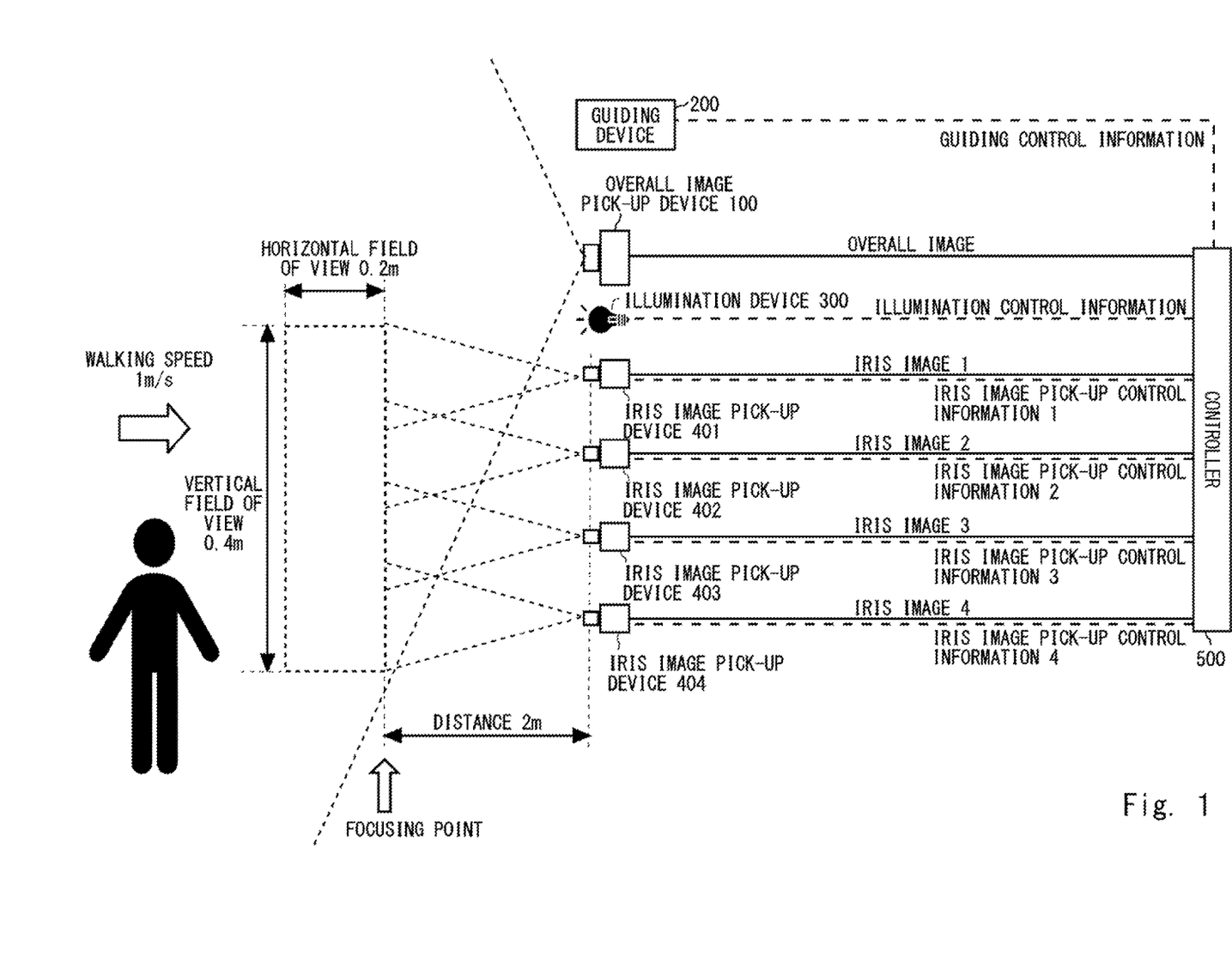
FIG. 1 is a block diagram showing an image pick-up system according to a first example embodiment of the present disclosure.

Example embodiments according to the present disclosure will be described hereinafter with reference to the drawings. FIG. 1 shows an image pick-up system according to a first example embodiment of the present disclosure. The image pick-up system includes an overall imaging device 100, a guiding device 200, an illumination device 300, iris image pick-up devices 401 to 404, and a controller 500. Note that although the number of iris image pick-up devices is four in FIG. 1, the number of iris image pick-up devices is not limited to any particular number. The number of iris image pick-up devices can be set as appropriate according to the field of view to be covered and the resolutions of available iris image pick-up devices.

The overall imaging device (overall image pick-up means) 100 photographs a subject with a wide field of view that is wide enough to cover a whole range of subjects from a tall subject to a short subject. The overall imaging device 100 may have a resolution in which a subject can be authenticated by his/her face.

The controller (control means) 500 monitors an overall image supplied from the overall imaging device 100, and controls the guiding device (guiding means) 200, the illumination device (illumination means) 300, and the plurality of iris image pick-up devices (iris image pick-up means) 401 to 404. The functions of the controller 500 can be implemented by hardware or by a computer program(s). The controller 500 determines a start of biometric authentication for the subject based on his/her overall image supplied from the overall imaging device 100, or based on an external input.

The control performed by the controller 500 includes at least one of guiding control, illumination control, or iris image pick-up control. In the guiding control, the controller 500 supplies guiding control information for guiding the subject to the guiding device 200. The guiding device 200 guides the subject based on the guiding control information. The guiding device 200 includes, for example, a display and/or a speaker(s). For example, the guiding device 200 presents an image(s) and a sound(s) for indicating the start of biometric authentication through the display and/or the speaker, respectively. Further, the guiding device 200 presents images and sounds for inducing the subject to turn his/her eyes to the iris image pick-up devices through the display and/or the speaker, respectively.

In the illumination control, the controller 500 supplies, to the illumination device 300, illumination control information for applying illumination light to the subject. The illumination device 300 applies light (e.g., near-infrared light) to the subject based on the illumination control information. The illumination device 300 includes LEDs (Light Emitting Diodes) as a light source, and a synchronization signal generator. The amount of light applied from the illumination device 300 to the subject is determined by the value of the current supplied to the LEDs, the lighting time of the LEDs, and the lighting cycle thereof, and the illumination control information includes the numerical values thereof. When the LEDs are not continuously kept in the on-state, the lighting cycle of the LEDs is synchronized with the frame rates of the plurality of iris image pick-up devices 401 to 404.

In the iris image pick-up control, the controller 500 determines, based on the overall image supplied from the overall imaging device 100, one of the plurality of iris image pick-up devices 401 to 404 that can suitably photograph an area of the subject including his/her eyes. Further, the controller 500 determines the vertical position of a region of interest that is read out at a high speed in the determined iris image pick-up device.

Figure 2:
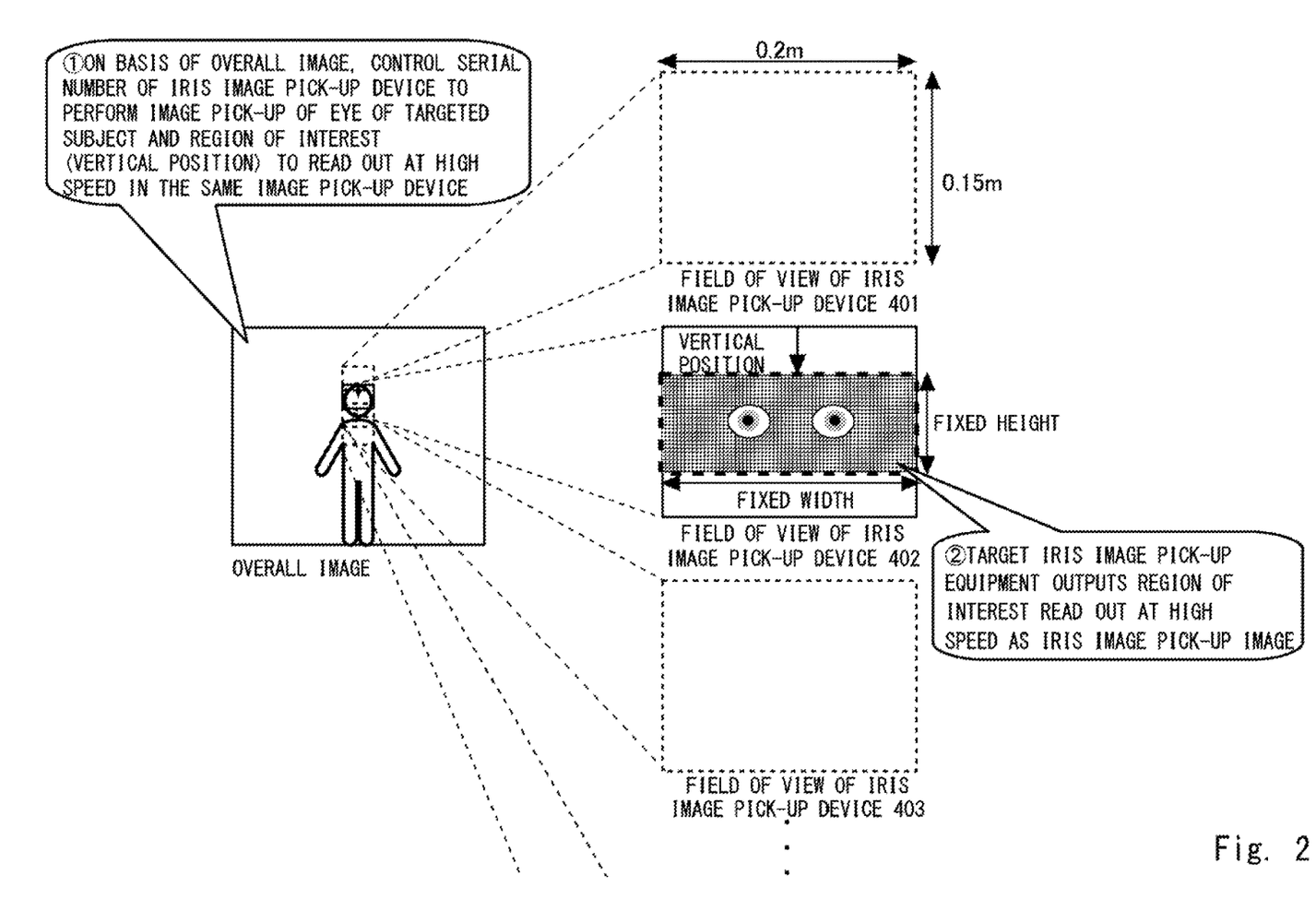
FIG. 2 shows a state of iris image pick-up control.

FIG. 2 shows a state of the iris image pick-up control. Details of the iris image pick-up control will be described with reference to FIG. 2. In this example, it is assumed that a general-purpose camera having 12 M pixels (4,000 horizontal pixels and 3,000 vertical pixels) and a frame rate of 60 fps is used for each of the iris image pick-up devices 401 to 404. Such cameras have been becoming widespread as industrial cameras. In the case where the photographing is performed with a granularity of 50 μm, with which a subject can be authenticated by his/her iris, the horizontal and vertical fields of view of each of the iris image pick-up devices are 0.2 m (4,000×50 [μm]=0.2 [m]) and 0.15 m (3,000×50 [μm]=0.15 [m]), respectively.

The plurality of iris image pick-up devices 401 to 404 are arranged so that they are stacked on top of each other in the vertical direction. Note that the plurality of iris image pick-up devices 401 to 404 are arranged so that the image areas of iris image pick-up devices adjacent to each other partially overlap each other. For example, the iris image pick-up devices 401 to 404 are arranged so that the image areas of iris image pick-up devices adjacent to each other overlap each other by 2.5 cm. In such a case, at the focusing point 2 m away from the four iris image pick-up devices, they can secure a field of view of 0.2 m in the horizontal direction and 0.45 m ((0.15-0.025)+(0.15-0.025-0.025)+(0.15-0.025-0.025)+(0.15-0.025)) m) in the vertical direction. That is, it is possible to secure the required field of view of 0.2 m in the horizontal direction and 0.4 m in the vertical direction. Note that it can be understood, by the drawings and the above description, that the iris image pick-up devices have the same fields of view as each other and are placed in positions different from each other.

In the case where the frame rate of each of the iris image pick-up devices is 60 fps, they cannot meet the required frame rate of 100 fps when they are used as they are. Note that an industrial camera or the like has a region-of-interest mode. In the region-of-interest mode, only a partial area that is defined as a region of interest is read out instead of reading out the entire area of the screen. It is possible to increase the frame rate by using such a region-of-interest mode.

The controller 500 sets a region of interest in any given iris image pick-up device and reads out the image in the region of interest from that iris image pick-up device. In the example shown in FIG. 2, a partial area of 4,000 pixels in the horizontal direction and 1,500 pixels in the vertical direction, which corresponds to a half of the entire area of the screen, is defined as the region of interest. In this case, since the number of pixels in each frame is a half of the number of pixels in the entire area, it is possible to increase the frame rate to 120 fps, which is twice the frame rate of 60 fps in the case where the entire area of the screen is read out. However, the horizontal and vertical fields of view of the partial area become 0.2 m and 0.75 m, respectively. Note that both eyes of a human being are aligned in the horizontal direction. Therefore, in the region-of-interest, it is preferred to reduce the number of pixels in the vertical direction, instead of reducing that in the horizontal direction, so that both eyes can be photographed.

Under the condition that the area of eyes is not photographed in the above-described range where the image areas of iris image pick-up devices adjacent to each other overlap each other, the iris image pick-up device that photographs the area of eyes is only one of the four iris image pick-up devices 401 to 404. Further, the condition under which the image can be read out at the frame rate of 120 fps is a partial area in that iris image pick-up device. The controller 500 infers one of the iris image pick-up devices 401 to 404 that can suitably photograph the area of eyes, and estimates the vertical position of the region of interest in which the image is read out at a high speed in that iris image pick-up device.

The above-described inference/estimation can be carried out by a method described below. The overall imaging device 100 has a resolution in which a subject can be authenticated by his/her face, and the controller 500 derives the positions of the eyes of the subject in the overall image taken by the overall imaging device 100. The controller 500 derives the iris image pick-up device corresponding to the positions of the eyes of the subject in the overall image and the positions of the eyes present in that imaging device by using camera parameters and the positional relation of the overall imaging device 100 and each of the iris image pick-up devices. By using the region-of-interest mode, it is possible, by using a general-purpose camera, to achieve a field of view wider than 0.2 m in the horizontal direction and 0.4 m in the vertical direction, and a temporal resolution higher than 100 fps.

Note that when the vertical position is changed in the above-described region-of-interest mode, a delay occurs before the start of the photographing. Therefore, in the above-described inference/estimation, an image that is obtained by photographing the subject at a position that is more distant than the position 2 meters away, i.e., more distant than the focusing point of the iris image pick-up device, e.g., by photographing the subject at a position 3 meters away may be used. The resolution in which a subject present at a position 3 meters away can be authenticated by his/her face can be achieved by a camera having about 2 M pixels, so that cameras having specifications lower than those of the iris image pick-up cameras can be used for the overall imaging device 100.

The controller 500 supplies iris image pick-up information to each of the iris image pick-up devices 401 to 404 based on the above-described iris image pick-up control. The controller 500 supplies iris image pick-up information including the vertical position of the region of interest to the iris image pick-up device that photographs the area of the eyes of the subject. The controller 500 may supply optional iris image pick-up information to the other iris image pick-up devices. The controller 500 may supply iris image pick-up information including information about the stop of the supply of the iris image to the other iris image pick-up devices, for example, in order to reduce the total amount of the data of the iris image.

Each of the iris image pick-up devices 401 to 404 supplies the iris image to the controller 500 based on the iris image pick-up information supplied from the controller 500. Note that each of the iris image pick-up devices 401 to 404 outputs the image in the region of interest that is set by the controller 500 by using the iris image pick-up information (i.e., the iris image) to the controller 500. Each of the iris image pick-up devices 401 to 404 may lossy-compress the iris image in the region of interest and output the compressed iris image to the controller 500. For example, each of the iris image pick-up devices 401 to 404 compresses the iris image in the region of interest by using quantization (pixel-by-pixel compression), predictive coding and quantization (compression on a basis of a plurality of pairs of pixels), or a combination of transform coding and quantization (compression on a basis of a plurality of pairs of pixels). The controller 500 performs the authentication and the registration described in the background section by using the iris images supplied from the iris image pick-up devices 401 to 404. The controller 500 returns to the next process when there is a next subject or when the authentication or the registration has failed.

Figure 3:
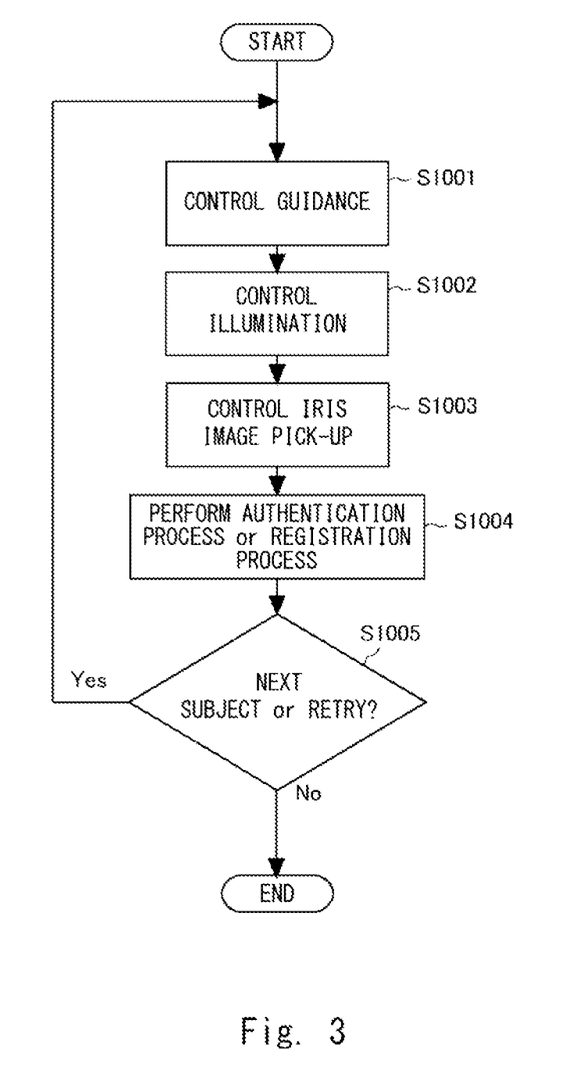
FIG. 3 is a flowchart showing an operational procedure in an image pick-up system.

Next, an operational procedure will be described. FIG. 3 shows an operational procedure in the image pick-up system. The controller 500 performs guiding control and thereby guides a subject by using the guiding device 200 (step S1001). The controller 500 performs the illumination control and thereby applies infrared light to the subject by using the illumination device 300 (step S1002). The controller 500 performs the above-described iris image pick-up control and thereby acquires an image(s) of an iris(es) (an iris image(s)) by using the plurality of iris image pick-up devices 401 to 404 (step S1003). The iris image(s) acquired in the step S1003 is used for the authentication or registration of the iris. In the step S1003, the controller 500 does not need to obtain the iris image from each of the iris image pick-up devices 401 to 404 for a given subject as described above. The controller 500 obtains the iris image from the iris image pick-up device that has photographed the area of the eyes of the subject.

The controller 500 performs iris-based authentication by using the iris image acquired in the step S1003, or registers the iris image (step S1004). The controller 500 determines whether or not there is a next subject, or whether or not re-authentication or re-registration should be performed (step S1005). When it is determined that there is a next subject, or re-authentication or re-registration should be performed, the process returns to the step S1001 and the process is performed starting from the guiding control.

Note that when the overall imaging device 100 according to this example embodiment has a resolution in which a subject can be authenticated by his/her face, and holds feature values for authenticating the subject by his/her face in a database but does not hold feature values for authenticating the subject by his/her iris in the database, the apparatus according to the present disclosure can also be used for a use in which the apparatus identifies a subject based on face-based authentication and registers extracted feature values of the iris(es) of the subject in the database. Further, the apparatus according to the present disclosure can also be used for a use in which the apparatus estimates information about the height of a subject based on information about the positions of the eyes obtained by the iris image pick-up control, or information about the positions of the eyes that is obtained when an iris image obtained by the iris image pick-up device is authenticated or registered, and registers the estimated information in the database. Further, the apparatus according to the present disclosure can be used, by using the estimated information about height, to determine or calibrate the vertical position of one of iris image pick-up devices that can suitably photograph the area of eyes and the region of interest in which the image is read out at a high speed in that iris image pick-up device.

In this example embodiment, a high resolution supporting the demanded 0.2 m×0.4 m field of view and a high frame rate performance corresponding to a time resolution of 0.01 s can be achieved with a combination of general-purpose cameras. As a result, it is easy to photograph an iris pattern at a level of quality sufficient for authentication and verification under conditions such as when there is a long distance between the subject and the image pick-up means, a wide field of view to be photographed, and the subject moves.

Figure 4:
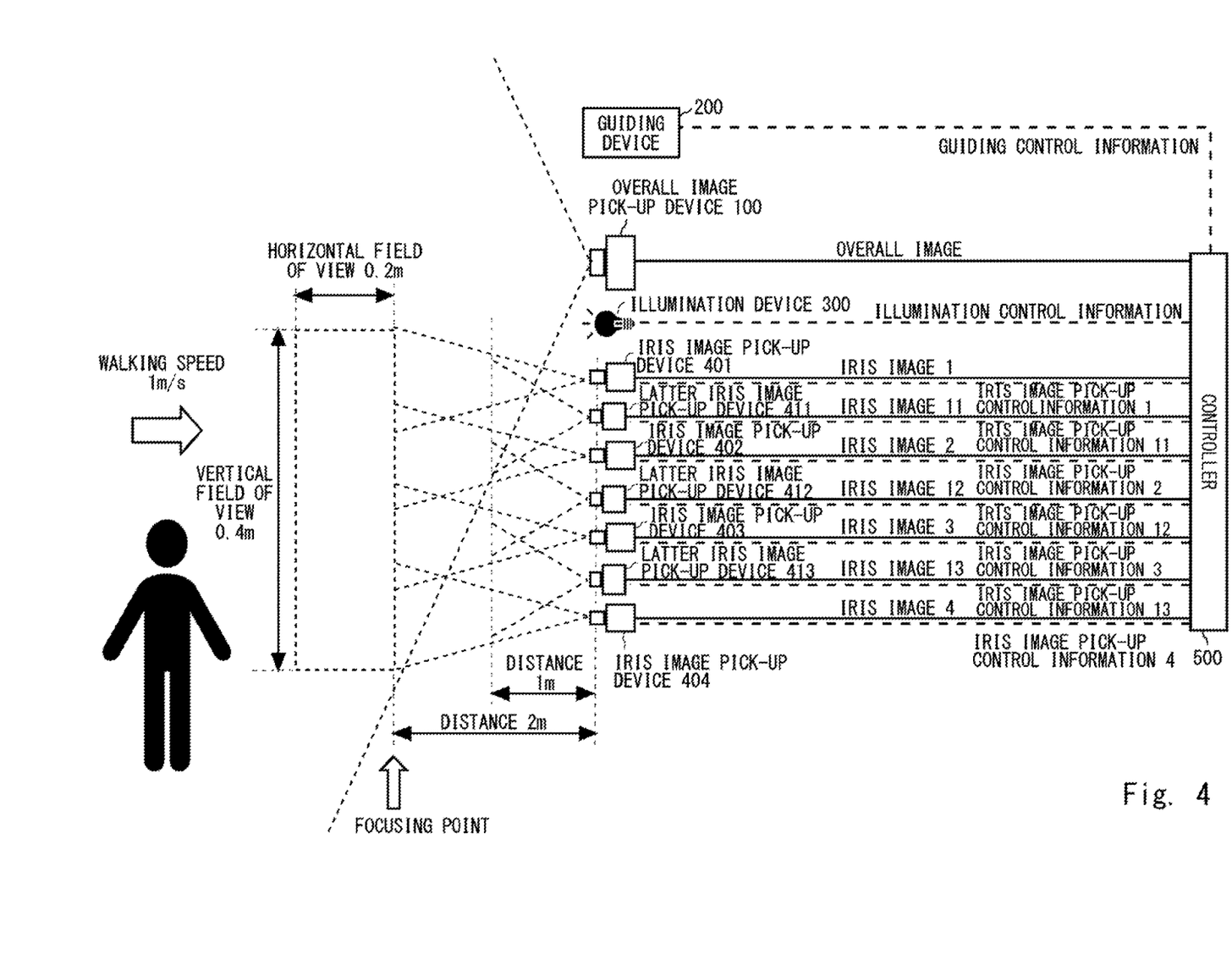
FIG. 4 is a block diagram showing an image pick-up system according to a second example embodiment of the present disclosure.

Next, a second example embodiment of the present disclosure will be described. FIG. 4 illustrates an image pick-up system according to the second example embodiment of the present disclosure. The image pick-up system according to this example embodiment includes latter iris image pick-up devices 411 to 413 in addition to the configuration of the image pick-up system according to the first example embodiment illustrated in FIG. 1. The latter iris image pick-up devices 411 to 413 are used to lower the retry rate of authentication or registration caused by the subject blinking or fluctuations in the eye position, for example. In this example embodiment, the iris image pick-up devices 401 to 404 and the latter iris image pick-up devices 411 to 413 form an image pick-up apparatus. The image pick-up apparatus may include an overall image pick-up device 100 and a controller 500. In this example embodiment, the controller 500 performs an image pick-up method using the iris image pick-up devices 401 to 404 and the latter iris image pick-up devices 411 to 413.

The latter iris image pick-up devices (second iris image pick-up means) 411 to 413 have a focusing point closer to the image pick-up position than the focusing point of the iris image pick-up devices (first iris image pick-up means) 401 to 404. The focusing point of the latter iris image pick-up devices 411 to 413 are set to positions at which the time difference between the time when the subject passes through the focusing point and the time when the subject passes through the focusing point of the iris image pick-up devices 401 to 404 is shorter than a blink interval described later and also longer than a blink duration. As an example, the focusing point of the iris image pick-up devices 401 to 404 is set 2 m away, and the focusing point of the latter iris image pick-up devices 411 to 413 is set 1 m away. In this example embodiment, the latter iris image pick-up devices 411 to 413 are each disposed between two adjacent iris image pick-up devices. The configuration of each of the latter iris image pick-up devices 411 to 413 may be similar to the configuration of the iris image pick-up devices 401 to 404, except for the different focusing point.

In this example embodiment, the controller 500 performs iris image pick-up control on the latter iris image pick-up devices 411 to 413 in addition to the control described in the first example embodiment. The controller 500 may perform the iris image pick-up control on the latter iris image pick-up devices 411 to 413 in the case where an image suitable for authentication and registration is not successfully acquired using the iris image pick-up devices 401 to 404, for example. Alternatively, the controller 500 may perform the iris image pick-up control on the latter iris image pick-up devices 411 to 413 regardless of whether or not an image suitable for authentication and registration is successfully acquired using the iris image pick-up devices 401 to 404, for example. The iris image pick-up control performed on the latter iris image pick-up devices 411 to 413 may be similar to the iris image pick-up control performed on the iris image pick-up devices 401 to 404, except for the different position of the subject.

Note that the latter iris image pick-up devices 411 to 413 and the iris image pick-up devices 401 to 404 have different focusing points because the lenses in the respective iris image pick-up devices have different focal lengths. In this example embodiment, the focusing point of the latter iris image pick-up devices 411 to 413 is in front of the focusing point of the iris image pick-up devices 401 to 404, and therefore lenses with short focal lengths are used in the latter iris image pick-up devices 411 to 413. In this example embodiment, the field of view of the latter iris image pick-up devices 411 to 413 using lenses with short focal lengths is wider than the field of view of the iris image pick-up devices 401 to 404.

Since blinking is a physiological phenomenon that is difficult to control even with the subject's own effort, there is a possibility that blinking may occur at the focusing point of the iris image pick-up devices 401 to 404. Humans blink an average of 20 times per minute (interval time 3 s) with each blink lasting 0.2 s (duration 0.2 s), and the time ratio of the eyes being open is 93.3%. Calculated simply, the retry probability for authentication and registration due to blinking is 6.6%, and approximately 7 out of 100 people will have to retry authentication or registration.

For example, if the subject is assumed to have a walking speed of 1 m/s, there is a time difference of 1 s between the time when the subject passes through the focusing point of the iris image pick-up devices 401 to 404 and the time when the subject passes through the focusing point of the latter iris image pick-up devices 411 to 413. This time difference of 1 s is shorter than the blink interval time of 3 s. Consequently, even if the subject is blinking at one of either the focusing point of the iris image pick-up devices 401 to 404 or the focusing point of the latter iris image pick-up devices 411 to 413, there is a high probability that the subject's eyes are open at the other. In this way, by using the latter iris image pick-up devices 411 to 413, the probability of successfully acquiring an image with the eyes open is increased dramatically. For this reason, the retry rate of authentication and registration caused by blinking can be lowered.

In the iris image pick-up devices 401 to 404, the eye region of the subject may be positioned at the boundary between the image pick-up regions of adjacent iris image pick-up devices in some cases. Head bobbing motion associated with walking is several centimeters, and as illustrated in the example of the first example embodiment, the vertical field of view that can be read out at 120 fps is only 7.5 cm. Consequently, in the case where the eye region of the subject is positioned at the boundary between the image pick-up regions of adjacent iris image pick-up devices, there is a possibility that the eye region may not be successfully covered by the region of interest due to head bobbing motion associated with walking.

In this example embodiment, the latter iris image pick-up devices 411 to 413 are respectively disposed between each of the iris image pick-up devices 401 to 404. The latter iris image pick-up devices 411 to 413 each perform image pick-up centered on a boundary region (an overlapping image region between adjacent iris image pick-up devices) of the images picked up by the iris image pick-up devices, for example. In this case, when one of the iris image pick-up devices 401 to 404 picks up an image of the eye region of the subject in the overlapping image region between adjacent iris image pick-up devices, the probability that the eye region will be captured at an optical central position by one of the latter iris image pick-up devices 411 to 413 is increased dramatically. Consequently, the retry rate of authentication and registration can be lowered, even in cases where the eye position fluctuates due to head bobbing motion associated with walking.

At this point, Patent Literature 1 discloses an iris authentication apparatus. The iris authentication apparatus described in Patent Literature 1 includes iris cameras that perform image pick-up of an iris of a person to be authenticated (subject), an illumination unit that provides illumination for iris image pick-up, a range sensor that measures the distance to the person to be authenticated, and a control unit for performing an iris authentication process using an image of the iris of the person to be authenticated. The iris authentication apparatus includes a plurality of iris cameras arranged in a vertical line. Further, the illumination unit is disposed at a position above the iris cameras and also higher than the person to be authenticated. In the iris authentication apparatus, a camera optical axis of the iris cameras and an irradiation region of the illumination unit are set to intersect at the focusing point of the iris cameras.

Patent Literature 1 describes that a re-authentication area is provided near the iris authentication apparatus as an area for re-authenticating a person to be authenticated who has failed iris authentication. The iris authentication apparatus further includes a second iris camera that performs image pick-up of the iris of the person to be authenticated in the re-authentication area, and a second illumination unit that provides illumination for iris image pick-up in the re-authentication area. Patent Literature 1 describes that the second iris camera for re-authentication is a close-up camera, while the iris cameras for ordinary authentication are long-shot cameras.

In comparison with Patent Literature 1, in Patent Literature 1, a subject who has failed authentication is led to the re-authentication area away from the walking path, and an image of the iris is acquired using the second iris camera in the re-authentication area. However, in Patent Literature 1, blinking by the subject in the re-authentication area is not considered. Consequently, there is a possibility that the subject may blink in the re-authentication area. As described above, blinking is difficult to control even with the subject's own effort. In Patent Literature 1, the probability that the subject will blink in the re-authentication area is roughly the same as the probability that the subject will blink in the ordinary authentication area.

In contrast, in this example embodiment as described above, even if the subject is blinking at one of either the focusing point of the iris image pick-up devices 401 to 404 or the focusing point of the latter iris image pick-up devices 411 to 413, there is a high probability that the subject's eyes are open at the other. Consequently, in this example embodiment, the retry rate of authentication and registration caused by blinking can be lowered compared to Patent Literature 1. Further, in this example embodiment, the latter iris image pick-up devices 411 to 413 are each disposed between two adjacent iris image pick-up devices, and perform image pick-up near the center of the field of view of the two adjacent iris image pick-up devices. Consequently, the retry rate of authentication and registration caused by fluctuations in the eye position can be lowered compared to Patent Literature 1.

Note that although the second example embodiment above describes an example in which the iris image pick-up devices 401 to 404 and the latter iris image pick-up devices 411 to 413 are used in the image pick-up apparatus, the image pick-up apparatus may be an apparatus which can perform image pick-up at two or more focusing points, and the image pick-up apparatus is not limited to the configuration described above. For example, the image pick-up apparatus may further include an iris image pick-up device having a focusing point at a different position from the focusing point of the iris image pick-up devices 401 to 404 and the focusing point of the latter iris image pick-up devices 411 to 413, and perform image pick-up at a total of three focusing points.

Note that although an example in which a partial area of 4,000 pixels in the horizontal direction and 1,500 pixels in the vertical direction is defined as the region of interest in FIG. 2, the present disclosure is not limited to this example. The shape of the region of interest is not limited to the rectangle, and the number of region of interest s is not limited to one. The controller 500 may, for example, derive the positions of the right eye and left eye of the subject from the overall image (the overlooked image) taken by the overall imaging device 100, and set a region of interest corresponding to the position of the right eye and a region of interest corresponding to the position of the left eye in the iris image pick-up device. In such a case, the iris image pick-up device supplies iris images of the right and left eyes to the controller 500. The shape of the region of interest may be rectangular or may be elliptic. The controller 500 may derive the positions of the right and left eyes of the subject based on the iris image taken by the iris image pick-up device instead of based on the overlooked image. For example, the controller 500 may temporarily define the partial area shown in FIG. 2 as the region of interest, and derive the positions of the right and left eyes from the images in the region of interest. In such a case, the controller 500 may set, based on the derived positions of the right and left eyes, each of a partial area corresponding to the position of the right eye and a partial area corresponding to the position of the left eye as a region of interest in the iris image pick-up device.

Figure 5:
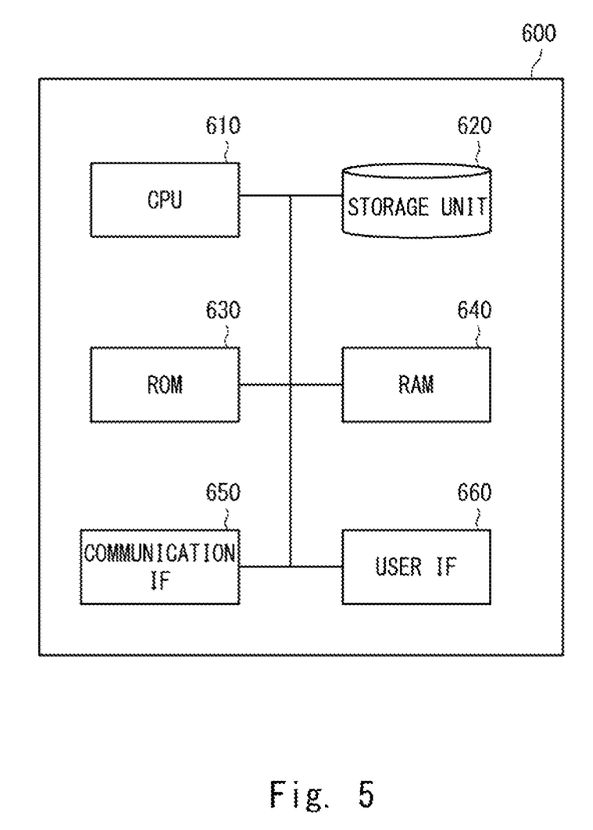
FIG. 5 is a block diagram showing an example of a configuration of a computer apparatus.

In each of above-described example embodiments, the controller 500 can be formed as a computer apparatus. FIG. 5 shows an example of a configuration of an information processing apparatus (a computer apparatus) that can be used for the controller 500. An information processing apparatus 600 includes a control unit (CPU: Central Processing Unit) 610, a storage unit 620, a ROM (Read Only Memory) 630, a RAM (Random Access Memory) 640, a communication interface (IF: Interface) 650, and a user interface 660.

The communication interface 650 is an interface for connecting the information processing apparatus 600 to a communication network through wired communication means, wireless communication means, or the like. The user interface 660 includes, for example, a display unit such as a display. Further, the user interface 660 includes an input unit such as a keyboard, a mouse, and a touch panel.

The storage unit 620 is an auxiliary storage device that can hold various types of data. The storage unit 620 does not necessarily have to be a part of the information processing unit 600, and may be an external storage device or a cloud storage connected to the information processing unit 600 through a network. The ROM 630 is a non-volatile storage device. For example, a semiconductor storage device such as a flash memory having relatively small capacity is used for the ROM 630. Programs executed by the CPU 610 can be stored in the storage unit 620 or the ROM 630.

The aforementioned program can be stored and provided to the information processing apparatus 600 by using any type of non-transitory computer readable media. Non-transitory computer readable media include any type of tangible storage media. Examples of non-transitory computer readable media include magnetic storage media such as floppy disks, magnetic tapes, and hard disk drives, optical magnetic storage media such as magneto-optical disks, optical disk media such as CD (Compact Disc) and DVD (Digital Versatile Disk), and semiconductor memories such as mask ROM, PROM (Programmable ROM), EPROM (Erasable PROM), flash ROM, and RAM. Further, the program may be provided to a computer using any type of transitory computer readable media. Examples of transitory computer readable media include electric signals, optical signals, and electromagnetic waves. Transitory computer readable media can provide the program to a computer via a wired communication line such as electric wires and optical fibers or a radio communication line.

The RAM 640 is a volatile storage device. As the RAM 640, various types of semiconductor memory apparatuses such as a DRAM (Dynamic Random Access Memory) or an SRAM (Static Random Access Memory) can be used. The RAM 640 can be used as an internal buffer for temporarily storing data and the like. The CPU 610 expands (i.e., loads) a program stored in the storage unit 620 or the ROM 630 in the RAM 640, and executes the expanded (i.e., loaded) program. By executing the program, the CPU 610 performs various types of control including, for example, guiding control, illumination control, and iris image pick-up control.

Although the present disclosure has been described with reference to example embodiments, the present disclosure is not limited to the above example embodiments. Various changes and modifications that can be understood by those skilled in the art can be made within the scope of the present disclosure in the configuration and details of the present disclosure.

For example, the whole or part of the example embodiments disclosed above can be described as, but not limited to, the following supplementary notes.

(Supplementary Note 1)

An image pick-up system comprising:
a plurality of iris image pick-up means disposed at mutually different positions in the same field of view;
overall image pick-up means for performing image pick-up over a wider field of view than the field of view of the iris image pick-up means;
guiding means for guiding a subject;
illumination means for illuminating the subject with light; and
control means for controlling, using an image from the overall image pick-up means, at least one of reading out an image from the plurality of iris image pick-up means, presenting at least one of an image and a sound through the guiding means, or providing illumination with light from the illumination means, wherein
the plurality of iris image pick-up means include
a plurality of first iris image pick-up means having a focusing point at a predetermined position and being for performing image pick-up of
mutually different regions in a vertical direction, and at least one second iris image pick-up means having a focusing point at a position closer to the first iris image pick-up means than the predetermined position, such that a time difference with respect to a time when the subject passes through the focusing point of the plurality of the first iris image pick-up means is shorter than a blink interval time and longer than a blink duration, and
the second iris image pick-up means is disposed between two adjacent first iris image pick-up means.

(Supplementary Note 2)

The image pick-up system according to Supplementary note 1, wherein
the control means performs readout of an image from the plurality of iris image pick-up means, and
in the readout of an image from the plurality of iris image pick-up means, the control means specifies an iris image pick-up means capable of performing image pick-up of an eye of the subject from among the plurality of iris image pick-up means on the basis of an image acquired by the overall image pick-up means, sets a region of interest including the position of the eye of the subject in the specified iris image pick-up means, and acquires an image of the region of interest from the specified iris image pick-up means.

(Supplementary Note 3)

The image pick-up system according to Supplementary note 1 or 2, wherein
two adjacent first iris image pick-up means have image pick-up ranges that partially overlap in the vertical direction, and
the second iris image pick-up means performs image pick-up of an image centered on the overlapping image pick-up range between the two adjacent first iris image pick-up means.

(Supplementary Note 4)

An image pick-up apparatus comprising:
iris image pick-up means for performing image pick-up of an iris of a moving subject, wherein
the iris image pick-up means includes
a plurality of first iris image pick-up means having a focusing point at a predetermined position and being for performing image pick-up of mutually different regions in a vertical direction, and
at least one second iris image pick-up means having a focusing point at a position closer to the first iris image pick-up means than the predetermined position, such that a time difference with respect to a time when the subject passes through the focusing point of the plurality of the first iris image pick-up means is shorter than a blink interval time and longer than a blink duration, and
the second iris image pick-up means is disposed between two adjacent first iris image pick-up means.

(Supplementary Note 5)

The image pick-up apparatus according to Supplementary note 4, wherein
two adjacent first iris image pick-up means have image pick-up ranges that partially overlap in the vertical direction, and
the second iris image pick-up means performs image pick-up of an image centered on the overlapping image pick-up range between the two adjacent first iris image pick-up means.

(Supplementary Note 6)

The image pick-up apparatus according to Supplementary note 4 or 5, wherein
the image pick-up means includes three or more of the first iris image pick-up means and two or more of the second iris image pick-up means, and
each of the two or more of the second iris image pick-up means is disposed between two adjacent ones of the first iris image pick-up means.

(Supplementary Note 7)

The image pick-up apparatus according to any one of Supplementary notes 4 to 6, wherein the second iris image pick-up means is disposed in a central position between two adjacent first iris image pick-up means.

(Supplementary Note 8)

The image pick-up apparatus according to any one of Supplementary notes 4 to 7, wherein
each of the first iris image pick-up means and the second iris image pick-up means includes a lens, and
a focal length of the lens in the second iris image pick-up means is shorter than the focal length of the lens in the first iris image pick-up means.

(Supplementary Note 9)

The image pick-up apparatus according to any one of Supplementary notes 4 to 8, further comprising:
overall image pick-up means for performing image pick-up over a wider range than an image pick-up range of the iris image pick-up means; and
control means for controlling an image readout from the first iris image pick-up means and an image readout from the second iris image pick-up means using an image picked up by the overall image pick-up means.

(Supplementary Note 10)

An image pick-up method comprising:
performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

(Supplementary Note 11)

An image pick-up method comprising:
performing image pick-up of an iris of a moving subject by using a plurality of first iris image pick-up means having a focusing point at a predetermined position and being for performing image pick-up of mutually different regions in a vertical direction; and
performing image pick-up of the iris of the subject by using at least one second iris image pick-up means having a focusing point at a position closer to the first iris image pick-up means than the predetermined position such that a time difference with respect to a time when the subject passes through the focusing point of the plurality of the first iris image pick-up means is shorter than a blink interval time and longer than a blink duration, and disposed between two adjacent first iris image pick-up means.

(Supplementary Note 12)

A non-transitory computer readable medium storing a program causing a computer to execute a process comprising:
performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

(Supplementary Note 13)

A non-transitory computer readable medium storing a program causing a computer to execute a process comprising:
performing image pick-up of an iris of a moving subject by using a plurality of first iris image pick-up means having a focusing point at a predetermined position and being for performing image pick-up of mutually different regions in a vertical direction; and
performing image pick-up of the iris of the subject by using at least one second iris image pick-up means having a focusing point at a position closer to the first iris image pick-up means than the predetermined position such that a time difference with respect to a time when the subject passes through the focusing point of the plurality of the first iris image pick-up is shorter than a blink interval time and longer than a blink duration, and disposed between two adjacent first iris image pick-up means.

This application is based upon and claims the benefit of priority from Japanese patent application No. 2019-026937, filed on Feb. 18, 2019, the disclosure of which is incorporated herein in its entirety by reference.

REFERENCE SIGNS LIST

100 OVERALL IMAGING DEVICE
200 GUIDE DEVICE
300 ILLUMINATION DEVICE
401-404 IRIS IMAGE PICK-UP DEVICE
411-413 LATTER IRIS IMAGE PICK-UP DEVICE
500 CONTROLLER
600 INFORMATION PROCESSING APPARATUS

What is claimed is:

1. An image pick-up system comprising:
a plurality of iris image pick-up cameras disposed at mutually different positions in a same field of view;
an overall image pick-up camera configured to perform image pick-up over a wider field of view than the same field of view of the iris image pick-up cameras;
a processor; and
a memory storing instructions executable by the processor to:
using an image from the overall image pick-up camera, reading out an image from the plurality of iris image pick-up cameras, wherein
the plurality of iris image pick-up cameras include:
three or more first iris image pick-up cameras having a focusing point at a predetermined position and configured to perform image pick-up of mutually different regions in a vertical direction, and
two or more second iris image pick-up cameras having a focusing point at a position closer to the first iris image pick-up cameras than the predetermined position, a distance between the focusing point of the first iris image pick-up cameras and the focusing point of the second iris image pick-up cameras being shorter than a distance that a person moves at a predetermined moving speed related to a moving speed of the person during a blink interval time related to a time interval between human blinks and longer than a distance that the person moves at the predetermined moving speed during a predetermined time related to duration of a blink,
each of the two or more of the second iris image pick-up cameras is disposed between two adjacent first iris image pick-up cameras.

2. The image pick-up system according to claim 1, wherein
the instructions are executable by the processor to, in the readout of the image from the plurality of iris image pick-up cameras:
specify an iris image pick-up camera capable of performing image pick-up of an eye of a subject from among the plurality of iris image pick-up cameras based on the image acquired by the overall image pick-up camera;
set a region of interest including a position of the eye of the subject in the specified iris image pick-up camera; and
acquire an image of the region of interest from the specified iris image pick-up camera.

3. The image pick-up system according to claim 1, wherein, for each of the two or more of the second iris image pick-up cameras:
the two adjacent first iris image pick-up cameras between which the second iris image pick-up camera is disposed have image pick-up ranges that partially overlap in the vertical direction, and
the second iris image pick-up camera performs image pick-up of an image centered on the overlapping image pick-up range between the two adjacent first iris image pick-up cameras between which the second iris image pick-up camera is disposed.

4. An image pick-up apparatus comprising:
a plurality of iris image pick-up cameras configured to perform image pick-up of an iris of a moving subject, wherein
the iris image pick-up cameras include:
three or more first iris image pick-up cameras having a focusing point at a predetermined position and configured to perform image pick-up of mutually different regions in a vertical direction, and two or more second iris image pick-up cameras having a focusing point at a position closer to the first iris image pick-up cameras than the predetermined position, a distance between the focusing point of the first iris image pick-up cameras and the focusing point of the second iris image pick-up cameras being shorter than a distance that a person moves at a predetermined moving speed related to a moving speed of the person during a blink interval time related to a time interval between human blinks and longer than a distance that the person moves at the predetermined moving speed during a predetermined time related to a duration of a blink, each of the two or more of the second iris image pick-up cameras is disposed between two adjacent first iris image pick-up cameras.

5. The image pick-up apparatus according to claim 4, wherein, for each of the two or more of the second iris image pick-up cameras:
the two adjacent first iris image pick-up cameras between which the second iris image pick-up camera is disposed have image pick-up ranges that partially overlap in the vertical direction, and
the second iris image pick-up camera performs image pick-up of an image centered on the overlapping image pick-up range between the two adjacent first iris image pick-up cameras between which the second iris image pick-up camera is disposed.

6. The image pick-up apparatus according to claim 4, wherein, for each of the two or more of the second iris image pick-up cameras:
the second iris image pick-up camera is disposed in a central position between the two adjacent first iris image pick-up cameras between which the second iris image pick-up camera is disposed.

7. The image pick-up apparatus according to claim 4, wherein
each first iris image pick-up camera and each second iris image pick-up camera includes a lens, and
a focal length of the lens in each second iris image pick-up camera is shorter than a focal length of the lens in each first iris image pick-up camera.

8. The image pick-up apparatus according to claim 4, further comprising:
an overall image pick-up camera configured to perform image pick-up over a wider range than an image pick-up range of the iris image pick-up camera;
a processor; and
a memory storing instructions executable by the processor to:
control an image readout from the first iris image pick-up cameras and an image readout from the second iris image pick-up cameras using an image picked up by the overall image pick-up camera.

9. An image pick-up method comprising:
performing, by a processor, image pick-up of an iris of a moving subject by using three or more first iris image pick-up cameras having a focusing point at a predetermined position and configured to perform image pick-up of mutually different regions in a vertical direction; and
performing, by the processor, the image pick-up of the iris of the subject by using two or more second iris image pick-up cameras having a focusing point at a position closer to the first iris image pick-up cameras than the predetermined position, a distance between the focusing point of the first iris image pick-up cameras and the focusing point of the second iris image pick-up cameras being shorter than a distance that a person moves at a predetermined moving speed related to a moving speed of the person during a blink interval time related to a time interval between human blinks and longer than a distance that the person moves at the predetermined moving speed during a predetermined time related to a duration of a blink, wherein
each of the two or more of the second iris image pick-up cameras is disposed between two adjacent first iris image pick-up cameras.

* * * * *